(12) United States Patent
Esser et al.

(10) Patent No.: US 11,730,527 B2
(45) Date of Patent: Aug. 22, 2023

(54) SURGICAL INSTRUMENT FOR TIGHTENING A BONE FIXATION MEMBER AROUND BONE

(71) Applicant: Stryker European Operations Limited, Carrigtwohill (IE)

(72) Inventors: Matthias Esser, Freiburg (DE); Daniel Gumpert, Denzlingen (DE); Gheorghe Marton, Freiburg (DE); Matthias Steffen, Merzhausen (DE)

(73) Assignee: Stryker European Operations Limited

( * ) Notice: Subject to any disclaimer, the term of this patent is extended or adjusted under 35 U.S.C. 154(b) by 230 days.

(21) Appl. No.: 17/089,128

(22) Filed: Nov. 4, 2020

(65) Prior Publication Data
US 2021/0128214 A1 May 6, 2021

(30) Foreign Application Priority Data
Nov. 4, 2019 (EP) ..................................... 19206931

(51) Int. Cl.
*A61B 17/88* (2006.01)
*A61B 17/82* (2006.01)

(52) U.S. Cl.
CPC ........ *A61B 17/8861* (2013.01); *A61B 17/823* (2013.01); *A61B 17/8863* (2013.01); *A61B 17/8869* (2013.01); *A61B 17/8872* (2013.01)

(58) Field of Classification Search
CPC ............ A61B 17/8861; A61B 17/8863; A61B 17/8869; A61B 17/8872; A61B 17/823; A61B 17/82
See application file for complete search history.

(56) References Cited

U.S. PATENT DOCUMENTS

| 3,438,406 | A | | 4/1969 | Rozmus |
| 3,610,296 | A | | 10/1971 | Kabel |
| 3,661,187 | A | * | 5/1972 | Caveney ............... B65B 13/027 D8/44 |
| 3,712,346 | A | | 1/1973 | Noorily |
| 3,752,199 | A | | 8/1973 | Fekete |
| 3,810,499 | A | | 5/1974 | Benfer |

(Continued)

FOREIGN PATENT DOCUMENTS

| DE | 1300465 B | 7/1969 |
| DE | 1919472 B2 | 8/1973 |

(Continued)

OTHER PUBLICATIONS

Extended European Search Report including Written Opinion for Application No. EP19206931.8, dated Apr. 17, 2020, pp. 1-6.

*Primary Examiner* — Amy R Sipp
(74) *Attorney, Agent, or Firm* — Lerner David LLP (57) ABSTRACT

Disclosed is a surgical instrument for tightening a bone fixation member around bone. The instrument comprises a body with a gripping portion extending from the body and configured to be grasped by a hand, a clamp for clamping a bone fixation member and a clamp carrier connected to and movably guided relative to the body. The clamp is connected to and movably guided relative to the clamp carrier. The instrument further comprises an actuator connected to and movably guided relative to the body, and configured to be operated by a hand, wherein the actuator is configured to move the clamp carrier via the clamp.

17 Claims, 8 Drawing Sheets

(56) References Cited

U.S. PATENT DOCUMENTS

| | | | |
|---|---|---|---|
| 4,064,918 | A | 12/1977 | Pobuta et al. |
| 4,570,340 | A | 2/1986 | Shaw |
| 4,688,607 | A * | 8/1987 | Wolcott ............... B65B 13/027 140/93.2 |
| 4,726,403 | A * | 2/1988 | Young .................. B65B 13/027 140/123.6 |
| 4,997,011 | A | 3/1991 | Dyer et al. |
| 5,057,113 | A | 10/1991 | Mingozzi |
| 6,206,053 | B1 | 3/2001 | Hillegonds |
| 7,063,110 | B2 | 6/2006 | Chen |
| 7,089,970 | B2 | 8/2006 | Bernard |
| 7,168,457 | B2 | 1/2007 | Bernard |
| 7,207,357 | B2 | 4/2007 | de Oliveira |
| 7,806,895 | B2 | 10/2010 | Weier et al. |
| 8,096,998 | B2 | 1/2012 | Cresina |
| 8,500,739 | B2 | 8/2013 | Schoutens et al. |
| 9,084,644 | B2 | 7/2015 | Knueppel |
| 9,345,465 | B2 | 5/2016 | Aldridge et al. |
| 9,351,765 | B2 | 5/2016 | Schoutens et al. |
| 10,307,196 | B2 | 6/2019 | Knueppel |
| 2002/0032450 | A1 * | 3/2002 | Trudeau ............ A61B 17/8869 606/103 |
| 2004/0059357 | A1 | 3/2004 | Koseki |
| 2006/0064110 | A1 | 3/2006 | Nesper et al. |
| 2009/0082776 | A1 | 3/2009 | Cresina |
| 2012/0067450 | A1 | 3/2012 | Shafer et al. |
| 2012/0197257 | A1 * | 8/2012 | Knueppel ......... A61B 17/8863 606/74 |
| 2013/0116736 | A1 | 5/2013 | De Oliveira |
| 2015/0305792 | A1 | 10/2015 | Knueppel |
| 2015/0313656 | A1 | 11/2015 | Hulliger |
| 2015/0342657 | A1 | 12/2015 | Voisard et al. |
| 2016/0287299 | A1 | 10/2016 | Lang |

FOREIGN PATENT DOCUMENTS

| | | |
|---|---|---|
| DE | 2214819 C3 | 12/1973 |
| DE | 2408201 A1 | 8/1974 |
| DE | 29612072 U1 | 9/1996 |
| DE | 10310004 B3 | 10/2004 |
| DE | 102011008778 A1 | 7/2012 |
| DE | 102011011778 A1 | 8/2012 |
| EP | 0299387 A1 | 1/1989 |
| EP | 299387 B1 | 2/1991 |
| EP | 0857466 B1 | 6/2002 |
| EP | 865334 B1 | 4/2004 |
| EP | 1564144 A2 | 8/2005 |
| EP | 1400448 B1 | 10/2005 |
| EP | 1108649 B1 | 5/2006 |
| EP | 1538083 B1 | 6/2008 |
| EP | 1897809 B1 | 5/2010 |
| EP | 2131771 B1 | 11/2010 |
| EP | 2670325 A1 | 12/2013 |
| EP | 1731109 B1 | 4/2014 |
| EP | 3137003 A1 | 3/2017 |
| EP | 2594217 B1 | 4/2017 |
| EP | 3148462 B1 | 4/2018 |
| WO | 2012040449 A1 | 3/2012 |
| WO | 2012106505 A1 | 8/2012 |
| WO | 2015167920 A1 | 11/2015 |
| WO | 2015183485 A1 | 12/2015 |

* cited by examiner

Fig. 7b

SURGICAL INSTRUMENT FOR TIGHTENING A BONE FIXATION MEMBER AROUND BONE

CROSS-REFERENCE TO RELATED APPLICATIONS

The present application claims priority from European Patent Application No. 19206931.8 filed Nov. 4, 2019, the disclosure of which is hereby incorporated herein by reference.

TECHNICAL FIELD

The present disclosure provides a surgical instrument for tightening a bone fixation member around bone.

BACKGROUND

WO 2012/106505 A1 describes an instrument for surgical use that assists tightening of a bone fixation member around bone, such as a sternum bone. This surgical instrument comprises a tension assembly and a cutter assembly.

SUMMARY

An underlying object is to provide a surgical instrument that improves versatility, reliability and handling of a surgical procedure in which a bone fixation member is tightened around bone.

According to a first aspect, the present disclosure provides a surgical instrument for tightening a bone fixation member around bone, comprising: a body with a gripping portion extending from the body and configured to be grasped by a hand; a clamp for clamping a bone fixation member; a clamp carrier connected to and movably guided relative to the body, wherein the clamp is connected to and movably guided relative to the clamp carrier; and an actuator connected to and movably guided relative to the body, and configured to be operated by a hand, wherein the actuator is configured to move the clamp carrier via the clamp.

The body may have a longitudinal extension along a longitudinal extension line, wherein the gripping portion may extend from the body at a central portion of the longitudinal extension of the body. Further, the longitudinal extension of the gripping portion may be orthogonal to the longitudinal extension of the body. The actuator may extend longitudinally in a plane defined by the longitudinal extension of the body and the longitudinal extension of the gripping portion.

The actuator may be mechanically linked to the clamp and by means of the clamp to the clamp carrier, and may be configured to first move the clamp before moving the clamp carrier. The clamp may be configured to be opened and/or closed by movement of the actuator while the clamp carrier remains stationary relative to the body.

The clamp may comprise two opposed clamping jaws which are configured to be movable by the actuator towards and/or away from each other. The clamping jaws may have opposed clamping surfaces which are correspondingly shaped in a non-planar manner. The clamping surfaces may be sinusoidal. The clamping jaws may be configured to provide frictional engagement with a bone fixation member.

The surgical instrument may be configured to amplify a force transmitted from the actuator to the clamping jaws by mechanical advantage. The mechanical advantage may be provided by a mechanical transmission, such as a multi-lever-assembly.

The clamp may comprise clamping arms and each of the clamping jaws may be pivotably hinged on one of the clamping arms. The clamping jaws may be hinged off-center along a longitudinal extension of the clamping arms. A first end of the clamping arms, which may be hinged by first axes on a lever arm, may be configured to be pivoted by the lever arm about a second end of the clamping arms, which may be hinged by second axes on the clamp carrier. The clamping jaws may be hinged on the clamping arms by intermediate axes which may be closer to the second axes than to the first axes.

The surgical instrument may comprise a ratchet mechanism. The ratchet mechanism may be connected to and movably guided relative to the body. In some variants, the ratchet mechanism is prestressed in a direction for engaging a bone fixation member. The clamp carrier may be movably guided relative to the ratchet mechanism and prestressed towards the ratchet mechanism, such that in its initial non-operated state, the clamp carrier may be configured to be in an initial position in which it abuts the ratchet mechanism and holds it in a given position against the prestress force of the ratchet mechanism. The clamp carrier may be prestressed by a biasing portion guided in a direction longitudinally along the longitudinal direction of the body. The biasing portion may comprise a resilient or flexible member, such as a spring, connected on one end to the body and on the other to the clamp carrier.

A first end of the actuator may be hinged on the gripping portion. A second end of the actuator opposite the first end may be configured to be pivoted relative to the gripping portion, wherein the second end of the actuator may be movably connected to a lever, which may be hinged on the body by an axis and connected to the clamp.

The body may comprise a receiving member configured to provide an abutment surface for one portion of a bone fixation member and guide another portion of the bone fixation member towards the clamp. The one portion may be a head portion while the other portion may be a tail portion of the bone fixation member, which may be a cable tie. The receiving member may comprise a curved mouth portion with lip-shaped protrusions configured to provide a curved funnel opening into the body. The receiving member may be movably hinged to the body.

The surgical instrument may comprise a limiting mechanism configured to engage the clamp carrier in order to limit its range of motion relative to the body in a direction towards a bone fixation member receiving end of the body, when the clamp carrier is moved a given distance relative to the body away from the bone fixation member receiving end of the body. Further optional features of such a limiting mechanism are provided in the following.

According to a second aspect, the present disclosure also provides a surgical instrument for tightening a bone fixation member around bone, comprising: a body with a gripping portion extending from the body and configured to be grasped by a hand; a clamp for clamping a bone fixation member; a clamp carrier, wherein the clamp is connected to and movably guided relative to the clamp carrier, wherein the clamp carrier is connected to and movably guided relative to the body along the body to and away from a bone fixation member receiving end of the body; and an actuator connected to and movably guided relative to the body, and configured to be operated by a hand to move the clamp and the clamp carrier relative to the body; and a limiting mechanism configured to engage the clamp carrier in order to limit a range of motion of the clamp carrier relative to the body in a direction towards the bone fixation member receiving end of the body, when the clamp carrier is moved a given distance relative to the body away from the bone fixation member receiving end of the body.

In an initial non-operated state, the limiting mechanism may be configured to be in a position and orientation capable of engaging the clamp carrier in order to limit the range of motion of the clamp carrier relative to the body in the direction towards the bone fixation member receiving end of the body. The limiting mechanism may be configured to be manually moved out of engagement with the clamp carrier. The limiting mechanism may be configured to be pressed to be moved out of engagement. The movement may comprise at least one if not both of a rotary and translatory movement. The limiting mechanism may be configured to be moved out of engagement by a single finger, such as a thumb, of a hand grasping the gripping portion in a position capable of operating the actuator. The limiting mechanism may protrude from a side of the body and may be prestressed from the inside of the body towards the side of the body from which it may protrude to be in a position capable of engaging the clamp carrier.

The limiting mechanism may comprise a first portion and a second portion. The first portion may be located within the body and the second portion may protrude from the body. The first portion may be fixed to or monolithic with the second portion. The second portion may protrude from a central portion of the body. The second portion may be formed as a button, optionally as a button with a corrugated surface.

The limiting mechanism may be arranged to lie on a longitudinal extension line of the actuator. In particular, the limiting mechanism may intersect the longitudinal extension line of the actuator. The second portion may lie closer to the gripping portion than the part of the actuator farthest away from the gripping portion. The second portion may further extend in a direction towards an intersection of the body and the gripping portion.

The limiting mechanism may be prestressed against the clamp carrier. As an example, the limiting mechanism may be prestressed against the clamp carrier in a direction orthogonal to a longitudinal extension line of the clamp carrier. The direction of prestress may be orthogonal to or along a plane defined by a longitudinal extension of the body and a longitudinal extension of the gripping portion.

The limiting mechanism and the clamp carrier may comprise corresponding engagement members. The engagement members may be tooth- or ramp-shaped. The tooth shape may be that of a rectangle. The ramp shape may be that of a triangle, optionally a right-angled triangle. The limiting mechanism and the clamp carrier may be configured to engage in a form-fit.

The surgical instrument of the second aspect may comprise a ratchet mechanism for engaging a bone fixation member. The ratchet mechanism may be hinged on the body. In some variants, the ratchet mechanism is movable between a first bone fixation member engagement position and a second bone fixation member disengagement position. The clamp carrier may be prestressed against the ratchet mechanism, holding the ratchet mechanism in its second position.

The limiting mechanism may be configured to engage the clamp carrier when the clamp carrier is moved away from the ratchet mechanism by a distance allowing the ratchet mechanism to move to its first position. Optionally, the limiting mechanism may be configured to engage the clamp carrier when the clamp carrier is moved away from the ratchet mechanism by a set larger distance than the distance allowing the ratchet mechanism to move to its first position.

The surgical instrument of the second aspect may comprise a cutter for cutting a bone fixation member. Features of such cutter are detailed in the following.

According to a third aspect, the present disclosure provides a surgical instrument for cutting a bone fixation member, comprising: a body with a gripping portion configured to be grasped by a hand, wherein the body has a bone fixation member receiving end; and a cutter for cutting a bone fixation member extending through the bone fixation member receiving end into the body, wherein the cutter comprises a cutting head with a cutting edge and a handling lever connected to the cutting head to actuate the cutting head, wherein one end of the handling lever is hinged on the body and the other end is free to be grasped by a hand; and a multi-lever-assembly connecting the handling lever and the cutting head, and configured to achieve mechanical advantage for an amplified cutting force of the cutting edge.

In some variants, the cutting force is amplified compared to a force exerted on the handling lever. In this way, the surgical instrument becomes easier to operate.

The mechanical advantage achieved by a mechanical amplification of a force exerted on the handling lever to a cutting force of the cutting edge may be provided by multiple lever stages of the multi-lever-assembly. The multi-lever-assembly may comprise a first lever stage and a second lever stage. Optionally, each lever stage may be configured to transform a rotational movement to a translational movement, or to transform a translational movement to a rotational movement. The movement transformation may alternate between successive lever stages.

The handling lever may form part of the first lever stage which may transform a rotational movement to a translational movement. The rotational movement of the handling lever may be limited such that the handling lever may not be rotated beyond a plane orthogonal to the longitudinal extension of the body, or the longitudinal extension line of the body, wherein this plane intersects the actuator at a point of the actuator in its initial non-operated state closest to the cutting head.

The first lever stage may comprise a transmission lever coupled to the handling lever, wherein the translational movement may be performed by the transmission lever along an extension direction of the body and transformed by the second lever stage to a rotational movement of the cutting head configured to cut a bone fixation member with its cutting edge. In particular, the translational movement may be performed by the transmission lever along a longitudinal extension line of the body. The surgical instrument may comprise a first opening leading to a cut-through opening of the cutting head for the bone fixation member to enter the body, and the transmission lever may comprise a second opening for the bone fixation member to exit from the body.

A holding member may be movably attached to the handling lever and configured to hold the handling lever to the body. In some cases, the holding member is configured to engage the body. The holding member may be arranged on a side of the surgical instrument opposite to the side of the surgical instrument containing the cutting head.

The holding member may be prestressed by means of a resilient member connecting the holding member and the handling lever. The holding member may be configured to be pressed to be moved out of engagement. The holding member may be configured to be moved out of engagement with the handling lever by a single finger, such as a thumb, of a hand grasping the gripping portion in a position capable of operating the actuator.

The holding member may be biased in a direction towards the other end of the handling lever. The holding member may comprise a first portion at least partially guided inside the handling lever. The holding member may have a range of motion relative to the handling lever limited only by the handling lever.

The handling lever may be prestressed in a direction away from the body. In some variants, the handling lever is hinged on a central portion of the body along a longitudinal axis of the body.

The cutter may comprise a cutting cylinder portion held in the body in a rotatable manner with an opening therethrough for receiving the bone fixation member to be cut. The cutter may comprise two openings in the form of clearance holes, one allowing the bone fixation member to enter and the other allowing the same bone fixation member to exit the surgical instrument.

The handling lever may be configured to remain within boundaries of the body. This may in particular be the case when held by the holding member in a given parallel orientation to the extension direction of the body.

According to a fourth aspect, the present disclosure provides a surgical instrument for cutting a bone fixation member, comprising: a body with a gripping portion configured to be grasped by a hand, wherein the body has a bone fixation member receiving end; a cutter for cutting a bone fixation member extending through the bone fixation member receiving end into the body, wherein the cutter comprises a cutting head and a handling lever connected to the cutting head, wherein one end of the handling lever is hinged on the body and the other end is free to be grasped by a hand; and a holding member movably attached to the handling lever and configured to hold the handling lever to the body, wherein the holding member is configured to engage the body.

The holding member may be arranged on a side of the surgical instrument opposite to the side of the surgical instrument containing the cutting head. The holding member may be prestressed by means of a resilient member connecting the holding member and the handling lever. The holding member may be configured to be pressed to be moved out of engagement. The holding member may be configured to be moved out of engagement with the handling lever by a single finger, such as a thumb, of a hand grasping the gripping portion in a position capable of operating the actuator.

The holding member may be biased in a direction towards the other end of the handling lever. The holding member may comprise a first portion at least partially inside the handling lever. The holding member may have a range of motion relative to the handling lever limited only by the handling lever.

The cutter may comprise a lever-assembly configured to achieve mechanical advantage for an amplified cutting force of the cutting head compared to a force exerted on the handling lever. Optionally, the cutter may comprise the multi-lever-assembly described above.

The lever-assembly may be configured to transform by a transmission lever a rotational movement induced by a hand through the handling lever hinged on the body to a substantially translational movement generally along a longitudinal axis of the body and further to a rotational movement by the cutting head configured to cut the bone fixation member.

The handling lever may be prestressed in a direction away from the body. The handling lever may be hinged on a central portion of the body along a longitudinal axis of the body. The rotational movement of the handling lever may be limited such that the handling lever may not be rotated beyond a plane orthogonal to the longitudinal extension of the body, or the longitudinal extension line of the body, wherein this plane intersects the actuator at a point of the actuator in its initial non-operated state closest to the cutting head.

The cutting head may comprise a cutting cylinder portion held in the body in a rotatable manner with an opening therethrough for receiving the bone fixation member to be cut. The cutting head may comprise two openings, one may allow the bone fixation member to enter and the other may allow the same bone fixation member to exit the surgical instrument.

The handling lever may be configured to remain within boundaries of the body, when held by the holding member in a given parallel orientation to the extension direction of the body.

The surgical instrument of the fourth aspect may also comprise a clamp for clamping the bone fixation member and a clamp carrier connected to and movably guided relative to the body. The clamp may be connected to and movably guided relative to the clamp carrier.

The surgical instrument may further comprise: a limiting mechanism configured to engage the clamp carrier in order to limit its range of motion relative to the body in a direction towards the bone fixation member receiving end of the body, when the clamp carrier is moved a given distance relative to the body away from the bone fixation member receiving end of the body.

The present disclosure further provides a surgical system, comprising: one of the aforementioned surgical instruments and a bone fixation member. The bone fixation member may be of a cable tie-type with or without teeth on one or two sides thereof, optionally on opposite sides thereof.

BRIEF DESCRIPTION OF THE DRAWINGS

The foregoing summary, as well as the following detailed description of the embodiments, will be better understood when read in conjunction with the drawings. It will be understood that the invention is not limited to the specific embodiments disclosed, and reference is made to the claims for that purpose. In the drawings:

FIG. 4a is a partial cross-sectional view from the side of the surgical instrument in its active state with the ratchet being permanently activated by an engaged state of a forward-movement limiter with a clamp carrier;

FIG. 4b is an enlarged cross-sectional view of the engagement between the limiter and the clamp carrier shown in FIG. 4a;

FIG. 5a is a partial cross-sectional view from the side of the surgical instrument in its inactive state with the ratchet being deactivated due to the forward-movement limiter being disengaged from the clamp carrier;

FIG. 5b is an enlarged cross-sectional view of the disengaged limiter shown in FIG. 5a;

FIG. 7b is an enlarged perspective cross-sectional view of the front of the surgical instrument and of the cutter head in the cutting state shown in FIG. 7a.

DETAILED DESCRIPTION

Figure 1:
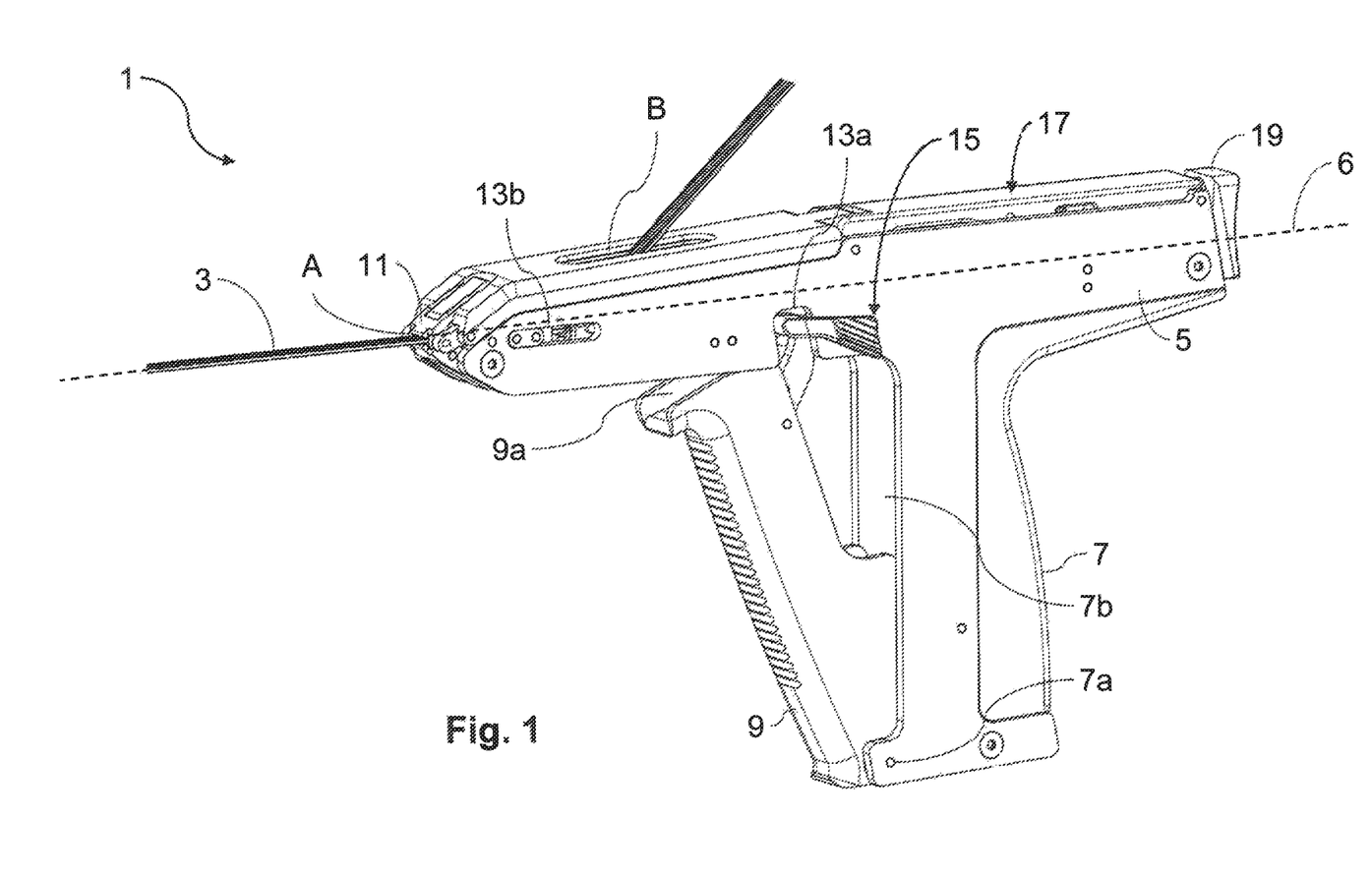
FIG. 1 is a perspective view of a surgical system comprising a surgical instrument and a bone fixation member inserted therein.

FIG. 1 shows a pistol-shaped surgical instrument 1 for tightening a bone fixation member 3 around bone, such as sternum bone. The bone fixation member 3 is inserted into the surgical instrument 1 at a front end and extends therethrough to exit the surgical instrument 1 at its top end.

The bone fixation member 3 is of the cable tie-type with a head portion (not shown) and a tail portion (shown) made of a flexible material with teeth on one side thereof—the upper side in FIG. 1. Typically, the tail portion of the bone fixation member 3 is wound around bone and inserted into the head portion of the bone fixation member 3. The part of the tail portion shown here is the one protruding from such head portion of the bone fixation member 3 when the bone fixation member 3 is wound around bone. Accordingly, this tail portion is referred to as the bone fixation member 3 for the purpose of describing the surgical instrument 1 in this disclosure.

The bone fixation member 3 is inserted into the surgical instrument 1 from the left in FIG. 1 though a first opening A and exits the surgical instrument 1 to the top in FIG. 1 though a second opening B. It should be noted that the bone fixation member 3 may very well lack any teeth typical for a cable tie due to the specific friction based—not form based—clamping of the bone fixation member 3 described below.

The surgical instrument 1 comprises a longitudinally directed body 5 extending from left to right in FIG. 1 along a longitudinal extension line 6. The surgical instrument 1 further comprises a longitudinal gripping portion 7 configured to be grasped by a hand and extending perpendicularly from the body 5. The gripping portion 7 is integral with the body 5. The gripping portion 7 comprises an opening 7a at its end furthest away from the body 5 and an internal space 7b. Of course, the surgical instrument 1 may comprise one single longitudinal body with the gripping portion being a portion along such body, i.e., not perpendicular but extending longitudinally along the body.

The surgical instrument 1 further comprises a trigger-like actuator 9. In this case, the actuator 9 comprises a recess 9a at its end facing the bone fixation member 3 and is movably connected to the body 5 and the gripping portion 7 at its opposite end.

The surgical instrument 1 has on its front of the body 5 a receiving member 11 for the bone fixation member 3 through which the bone fixation member 3 first passes when being inserted—from left to right in FIG. 1—into the body 5 of the surgical instrument 1. The receiving member 11 may either be rigidly connected to the body 5 and even be integral with the body 5, or it may be movably hinged to the body 5 in order to adapt to different angles of operation.

Along its left side, the body 5 comprises a first lateral opening 13a through which a limiting mechanism 15 protrudes in order to be displaced by the user's thumb when the user grips the gripping portion 7 to operate the actuator 9. The limiting mechanism 15 is similarly located as a pistol slide stop/release on the body 5, i.e., at a central portion of the longitudinal extension of the body 5 and/or at a portion of the body 5 from which the gripping portion 7 extends. In this regard, the gripping portion 7 may extend from the body 5 at an end of the body 5 opposite to the end of the body 5 comprising the receiving member 11. The body 5 further comprises a second lateral opening 13b for guiding and indication purposes.

The surgical instrument 1 comprises along its top edge a cutter mechanism 17, further referred to as cutter 17. The cutter 17 is held in place (i.e., in abutment with the body 5) by a holding member 19, which is brought in selective engagement with the back of the body 5 opposite the receiving member 11. The holding member 19 is prestressed into a first position in which it holds the cutter 17 in an initially inoperable state. The holding member 19 can be displaced against the prestressing force by the user's thumb, when the user grips the gripping portion 7 in order to operate the actuator 9, into a position in which the holding member 19 releases the cutter 17 into an operable state.

Figures 2A, 2B:
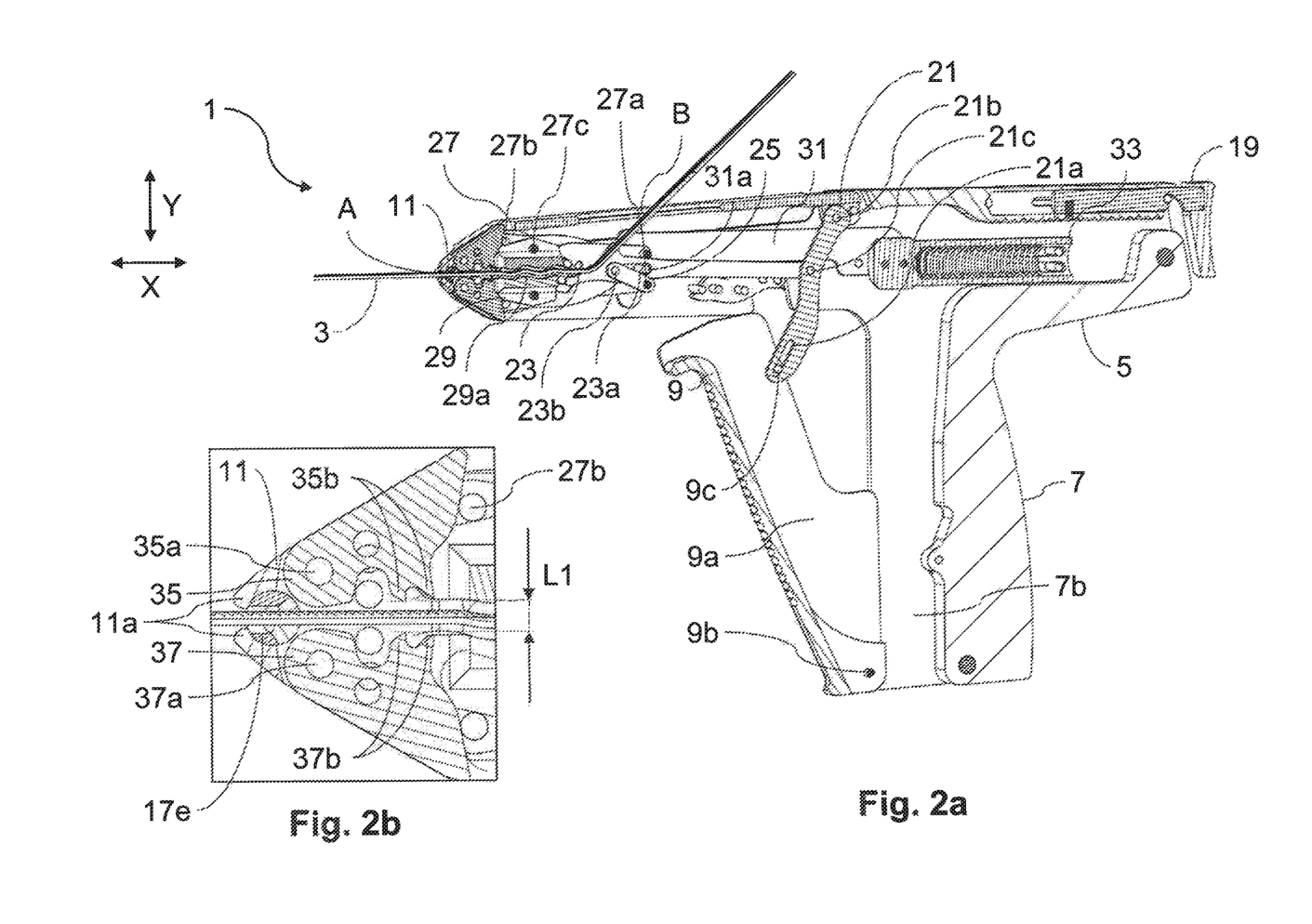
FIG. 2a is a cross-sectional view from the side of the surgical instrument in its inactive state in which the bone fixation member is inserted therein from the left and exits therefrom from the top.
FIG. 2b is an enlarged cross-sectional view of the front end of the surgical instrument shown in FIG. 2a with an inactive double-sided ratchet.

FIG. 2a shows a longitudinal cross-section through surgical instrument 1 and the actuator 9 having a U-shaped cross-section, see FIG. 1, with a back recess 9a along the entire length of the actuator 9 from top to bottom. In the recess 9a a first axis 9b extends laterally between parallel walls at a bottom end of the actuator 9, which bottom end is facing away from the body 5. A second axis 9c extends parallel to the first axis 9b at the opposite, top end of the actuator 9, which top end is close to the body 5. The actuator 9 is pivotably hinged to the gripping portion 7 by means of the first axis 9b such that the actuator 9 can pivot into or away from the internal space 7b of the opposed larger U-shaped gripping portion 7. A bottom back portion of the actuator 9 or the entire actuator 9 may always remain inside the internal space 7b.

The second, top axis 9c is received in a balance beam shaped longitudinal lever 21, more specifically in a elongate hole 21a thereof which extends at one end of the lever 21 in its longitudinal direction. The lever 21 is hinged on its opposite end to the body 5 by means of an axis 21b.

Between the elongate hole 21a and the axis 21b, the lever 21 is hinged via an axis 21c to a back of a longitudinal force transmitting member 23. The longitudinal force transmitting member 23 extends towards the front of the body 5 and towards the receiving member 11 in a longitudinal direction of the body 5. The force transmitting member 23 comprises on its front—opposite its back—an elongate hole 23a extending in the longitudinal direction of the force transmitting member 23 followed by an axis 23b closer to the front of the force transmitting member 23 than the elongate hole 23a. The axis 23b hinges a top (not shown) and a bottom (shown) longitudinal lever arm 25 at first ends thereof to the front of the force transmitting member 23.

The lever arms 25 on second ends thereof opposite their first ends are connected to clamp arms 27 via first axes 27a on first ends of the clamp arms 27. The clamp arms 27 have a non-linear shape and cross each other in FIG. 2a. However, the clamp arms 27 could very well have a linear shape and not cross each other. The second ends of the clamp arms 27 opposite the first ends have second axes 27b. Between the respective first axes 27a and second axes 27b and the respective first and second ends of the clamp arms 27, there are parallel intermediate axes 27c on the clamp arms 27. These intermediate axes 27c are closer to the second axes 27b than to the first axes 27a.

The intermediate axes 27c hinge clamp jaws 29 pivotably to the clamp arms 27. The clamp jaws 29 each have a cross-section in the shape of an isosceles triangle. Both clamp jaws 29 have non-planar, curved (e.g., sinusoidally shaped) clamping surfaces 29a. These surfaces 29a face each other and assume a first distance in the inactive state of the surgical instrument 1 illustrated in FIG. 2b. In other words, the force transmitting member 23, the longitudinal lever arm 25, the clamp arms 27 and the clamp jaws 29 form a clamp for clamping the bone fixation member 3.

The clamp arms 27 are hinged by the second axes 27b to a longitudinal clamp carrier 31, in particular on a first end of the clamp carrier 31 closest to the front of the body 5 and the receiving member 11. The clamp carrier 31 extends longitudinally in a front-to-back direction of the body 5. It is connected and movably guided relative to the body 5. The clamp carrier 31 comprises a pin 31a which is received in the elongate hole 23a of the force transmitting member 23 as guidance for the force transmitting member 23. The clamp carrier 31 is movably connected to the body 5 on its first end by means of a guiding block movably held in the second lateral opening 13b of the body 5—see FIG. 1—to be displaceable in the longitudinal direction of the body 5. On its second end closest to the back of the body 5 and opposite the first end, the clamp carrier 31 is held by means of a biasing (i.e., prestressing) portion 33 guided in a direction X longitudinally along the body 5.

FIG. 2b shows that the clamp carrier 31 with a front thereof is prestressed against a double-sided ratchet mechanism with two ratchet members 35, 37. These ratchet members 35, 37 are hinged on the receiving member 11 via respective axes 35a, 37a and prestressed towards each other. Alternatively, the ratchet members 35, 37 can be hinged to the body 5 or otherwise. Respective ratchet teeth 35b, 37b of the ratchet members 35, 37 are located opposite each other and inclined towards the clamp carrier 31 and away from the front of the body 5. The clamp carrier 31 is prestressed towards the ratchet members 35, 37 and abuts the ratchet members 35, 37 to hold them in an open, initial non-operated state in which the ratchet teeth 35b, 37b remain a first distance L1 away from each other. This distance L1 should be larger than the thickness of the bone fixation member 3 used in order to prevent engagement of the teeth of the bone fixation member 3 with the ratchet teeth 35b, 37b of the ratchet members 35, 37 for an easier insertion of the bone fixation member 3 into the surgical instrument 1.

Figure 2C:
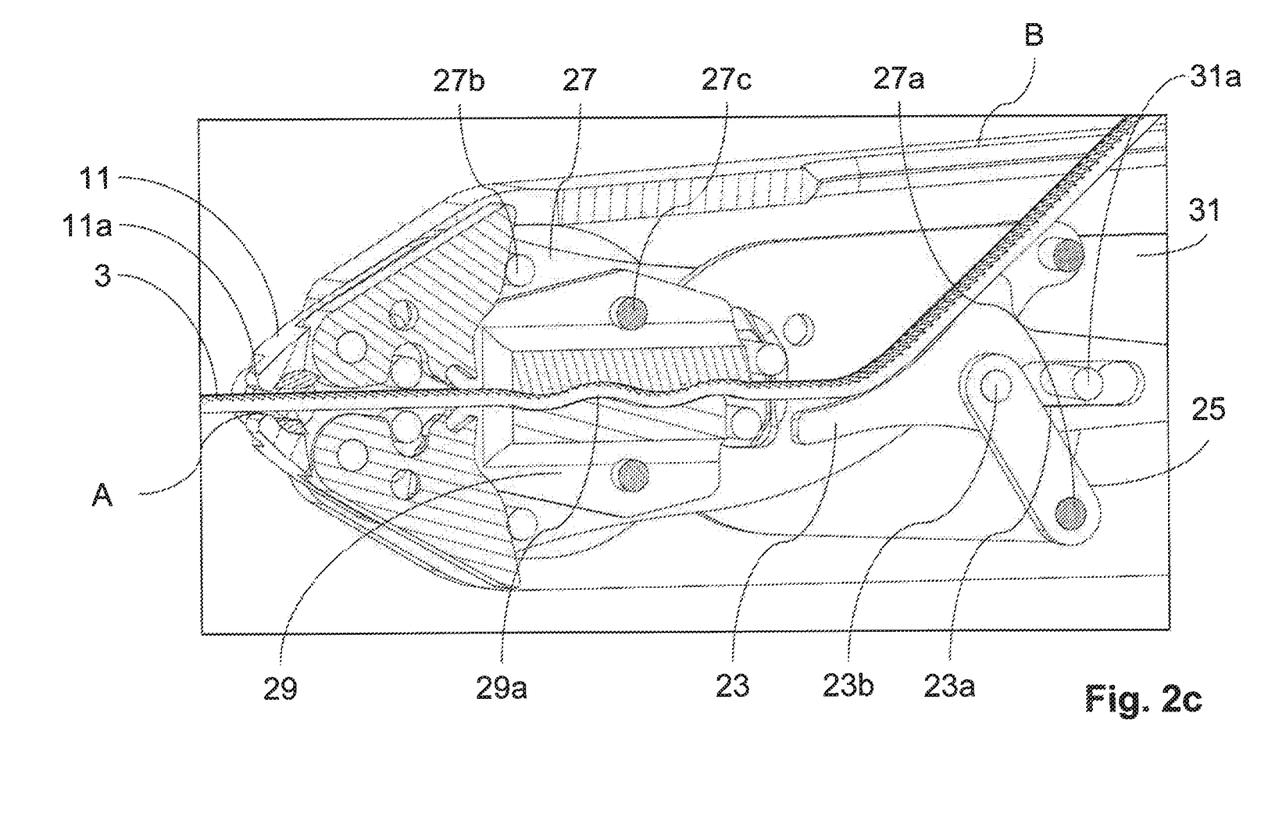
FIG. 2c is another enlarged cross-sectional view of the front end of the surgical instrument shown in FIG. 2a with a clamp for tensioning.

FIG. 2c shows an enlarged view of the front of the surgical instrument 1 shown in FIG. 2a. The receiving member 11 comprises a curved mouth portion with lip-shaped protrusions 11a—see FIG. 2c—configured to provide a curved funnel-like opening A into the body 5 of the surgical instrument 1. The lip shaped protrusions 11a serve the purpose to abut against the head portion (not shown) of the bone fixation member 3 and guide the tail portion of the bone fixation member 3 shown in the figures towards the clamp.

Figures 3A, 3B:
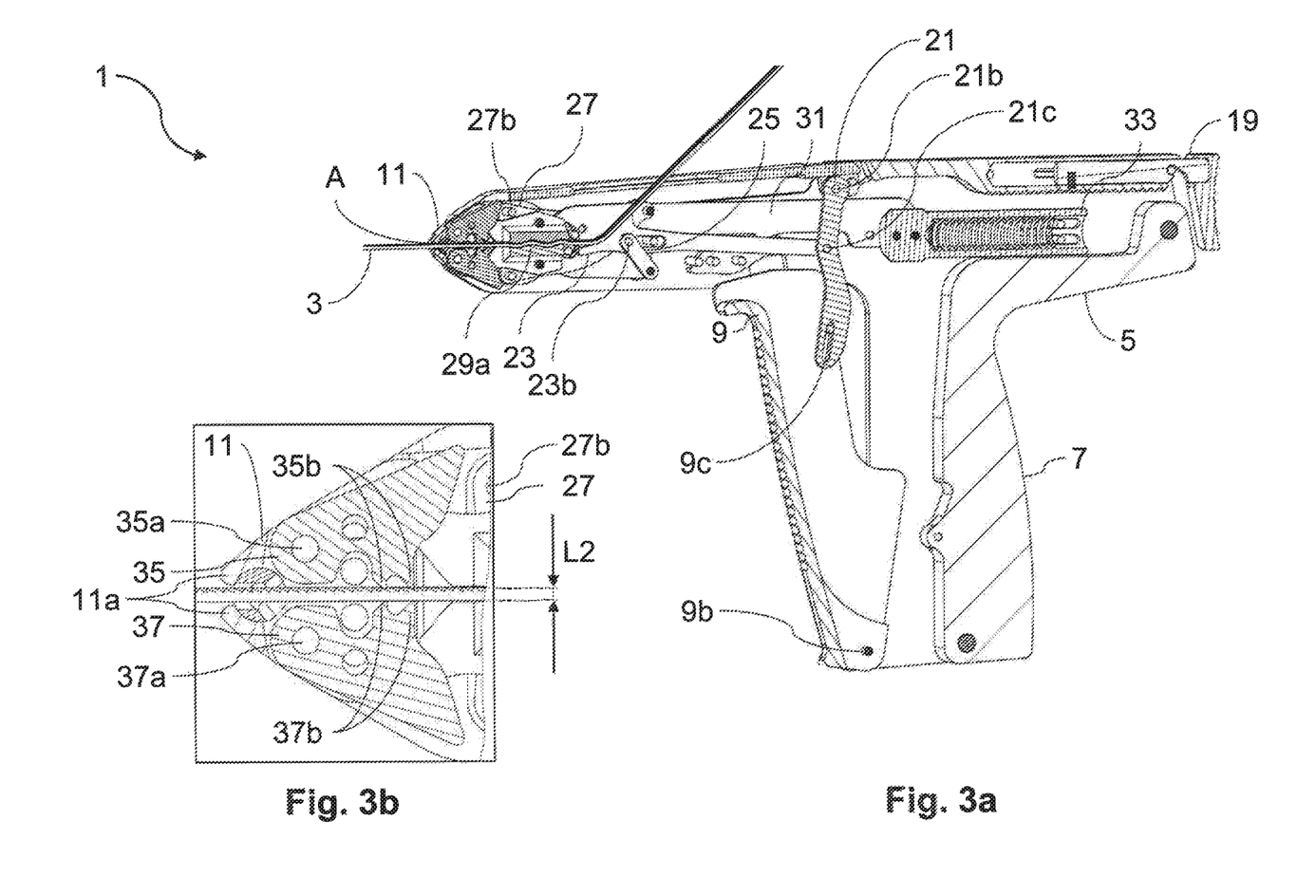
FIG. 3a is a cross-sectional view from the side of the surgical instrument in its active state in which the bone fixation member is held firmly by the clamp for tensioning.
FIG. 3b is an enlarged cross-sectional view of the front end of the surgical instrument shown in FIG. 3a with an active double-sided ratchet.

FIG. 3a shows an active state of the surgical instrument 1. In this active state, the actuator 9 is pivoted about the first axis 9b in a clockwise direction towards the gripping portion 7 by the force exerted on the actuator 9 through a user's hand gripping the gripping portion 7 and pulling the actuator 9 towards the gripping portion 7 with his or her fingers. The lever 21 is pivoted by the second axis 9c of the actuator 9 in a counter-clockwise direction about the top axis 21b of the lever 21. Consequently, the force transmitting member 23 is pulled via the connecting axis 21c of the lever 21 towards the back of the body 5 and away from the receiving member 11. The lever arms 25 are pivoted about the axis 23b of the force transmitting member 23 and pivot the clamp arms 27 about their second axes 27b on the clamp carrier 31. Thereby, the clamp arms 27 bring the clamping surfaces 29a of the clamp jaws 29 closer under overall mechanical advantage compared to the initial hand-force exerted on the actuator 9 by the user. The approximated clamp jaws 29 are configured to provide pure frictional engagement with the bone fixation member 3 therebetween.

The further movement of the actuator 9 towards the gripping portion 7 leads to the state of the surgical instrument 1 shown in FIG. 3a. In this state, the clamp carrier 31 is displaced backwards relative to the receiving member 11 via its connection by the second axes 27b with the clamp arms 27 against the prestress force of the biasing member 33. Thereby, the bone fixation member 3 is pulled into the body 5, which may cause the bone fixation member 3 to be tightened around bone (not shown).

The above described arrangement ensures that the clamp carrier 31 remains stationary relative to the body 5 while the clamp can be closed or opened. This allows the clamp carrier 31 to use its entire range of motion within the body 5 for pulling the bone fixation member 3 into the body 5. Thereby, efficiency of the surgical instrument 1 with regard to its tightening ability is improved, since no range of motion of the clamp carrier 31 is wasted for the actual clamping and unclamping of the bone fixation member 3.

FIG. 3b shows that as soon as the front of the clamp carrier 31 no longer abuts against the ratchet members 35, 37, i.e., the clamp carrier 31 is in an operated state, the prestressed ratchet members 35, 37 pivot about their respective axes 35a, 37a automatically towards each other such that the ratchet teeth 35b, 37b move towards each other to a second distance L2 there between only limited by the thickness of a bone fixation member 3 there between. Preferably, the second distance L2 is less than the first distance L1.

Figures 4A, 4B:
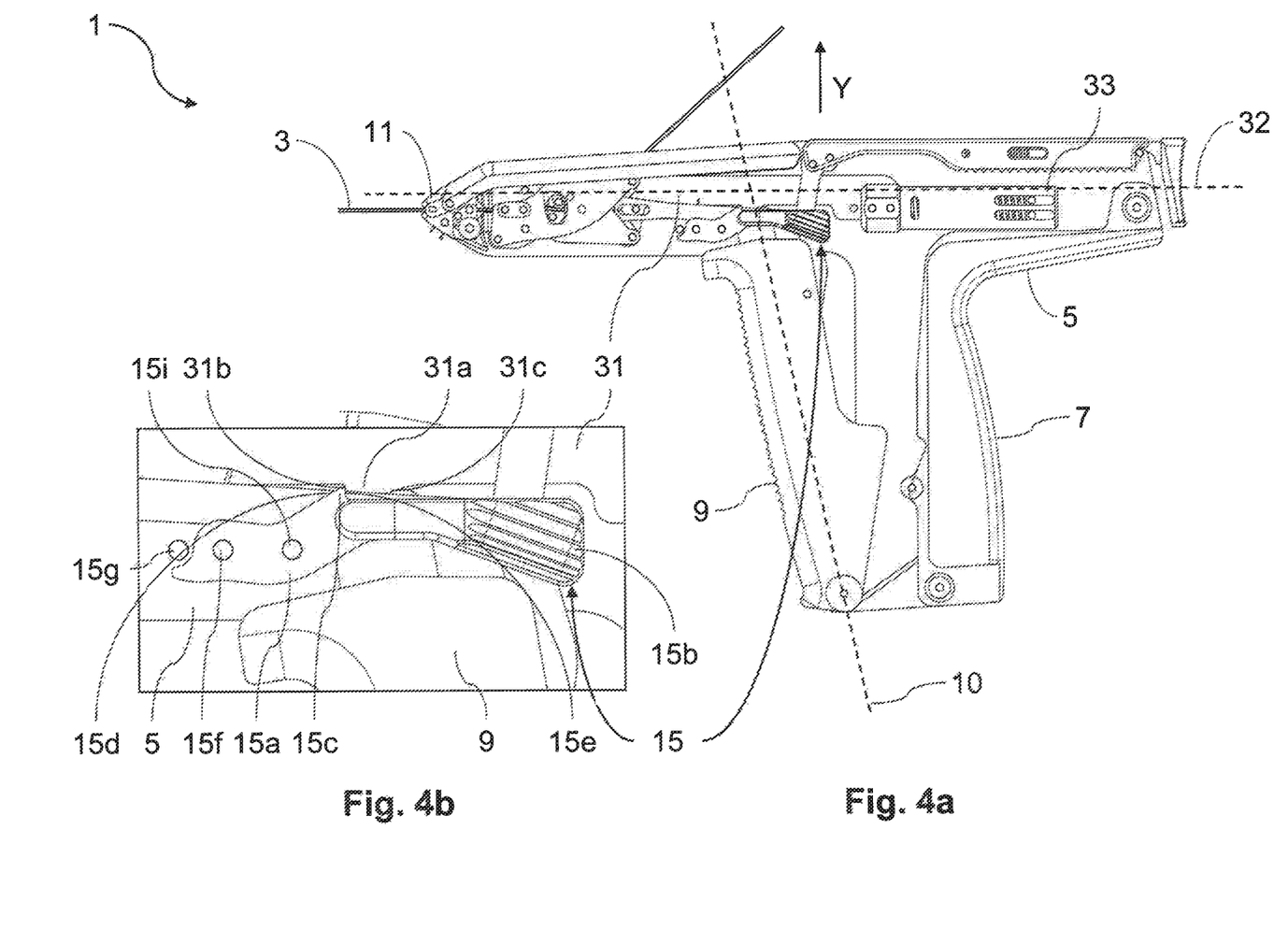

FIG. 4a shows a clamp carrier moving state of the surgical instrument 1 in which the actuator 9 is pulled towards the gripping portion 7 beyond a state in which the clamp is closed, i.e. a state after the state shown in FIG. 3a. FIG. 4b shows that the clamp carrier 31 comprises a bottom protrusion 31a with a perpendicular face 31b on one side, i.e., the side directed towards the front of the body 5 and the receiving member 11, and a sloping face 31c on the opposite side, i.e., the side directed towards the back of the body 5 opposite the receiving member 11.

The limiting mechanism 15 intersects a longitudinal extension line 10 of the actuator, see FIG. 4a. The limiting mechanism 15 comprises a first portion 15a and a second portion 15b. The first portion 15a is hidden within the body 5 and the second portion 15b, here in the shape of a corrugated button, extends laterally from the body 5—see FIG. 1. The first and second portions 15a and 15b are fixed to each other. The first portion comprises a top protrusion 15c, which is similarly shaped as the bottom protrusion 31a and configured to engage in a form-fit with the bottom protrusion 31a of the clamp carrier 31. In particular, the top protrusion 15c has a sloping face 15d on one side, i.e., the side directed towards the front of the body 5 and the receiving member 11, and a perpendicular face 15e on the opposite side, i.e., the side directed towards the back of the body 5 opposite the receiving member 11. In a longitudinal direction of the limiting mechanism, the top protrusion 15c is located between the second portion 15b and a pivot axis 15f.

The entire limiting mechanism 15 is configured to pivot about the pivot axis 15f. The pivot motion of the limiting mechanism 15 is limited clockwise in FIG. 4b by a pivot stop 15g fixed to the body 5 and counterclockwise by the clamp carrier 31. The limiting mechanism 15 is prestressed towards the clamp carrier 31 by means of a resilient member, which in this case is a coil spring 15h—see FIG. 6a—wound about the pivot axis 15f with its ends fixed to the pivot stop 15g and a fixation point 15i of the limiting mechanism 15. Here, the fixation point 15i is another axis fixed to the first portion 15a of the limiting mechanism 15. Notice that the ends of the coil spring 15h are not properly located in FIG. 6a, since they should be below the stop pin 15g and below the fixation point 15i. As such, it is evident that the protrusions 15c and 31a are permanently arranged in one plane.

In the state of FIG. 4a, the top protrusion 15c of the limiting mechanism 15 provides a form-fit stop to the bottom protrusion 31a of the clamp carrier 31. This limits the travel distance of the clamp carrier 31 in a direction towards the front of the body 5 and the receiving member 11. Thereby, it is ensured that the ratchet teeth 35b, 37b of the ratchet members 35, 37 are constantly urged towards each other to engage a bone fixation member 3 there between as shown in FIG. 3b during multiple operational movements of the actuator 9 for incrementally tightening the bone fixation member 3 around bone. In other words, as long as the limiting mechanism 15 is engaged, the ratchet mechanism remains active.

Figures 5A, 5B:
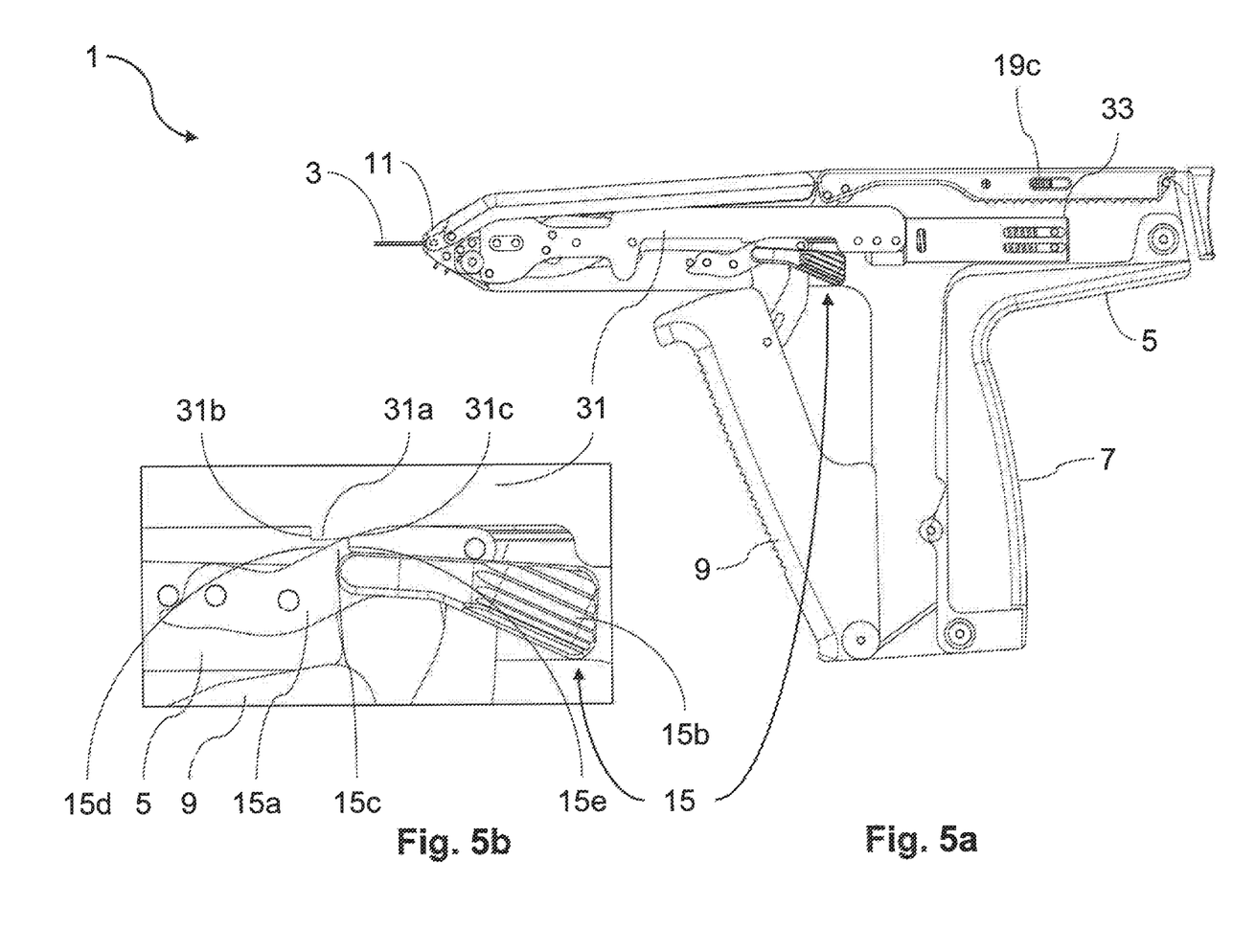

FIGS. 5a and 5b show a state prior to the state of the surgical instrument 1 shown in FIGS. 4a and 4b, wherein, in the state of FIGS. 5a and 5b, the top protrusion 15c of the limiting mechanism 15 is urged against and abuts the sloping face 31c of the bottom protrusion 31a of the clamp carrier 31. A further displacement of the actuator 9 towards the gripping portion 7 will result in the state shown in FIGS. 4a and 4b, in which the top protrusion 15c of the limiting mechanism 15 snaps in front of the bottom protrusion 31a of the clamp carrier 31. Thereby, their respective perpendicular faces 15e and 31b engage in a form-fit to limit the displacement of the clamp carrier 31 in a back-to-front direction. In order to disengage the limiting mechanism 15 from the clamp carrier 31, the second portion 15b of the limiting mechanism 15 has to be manually pushed towards the gripping portion 7 and/or away from the clamp carrier 31.

Figures 6A, 6B:
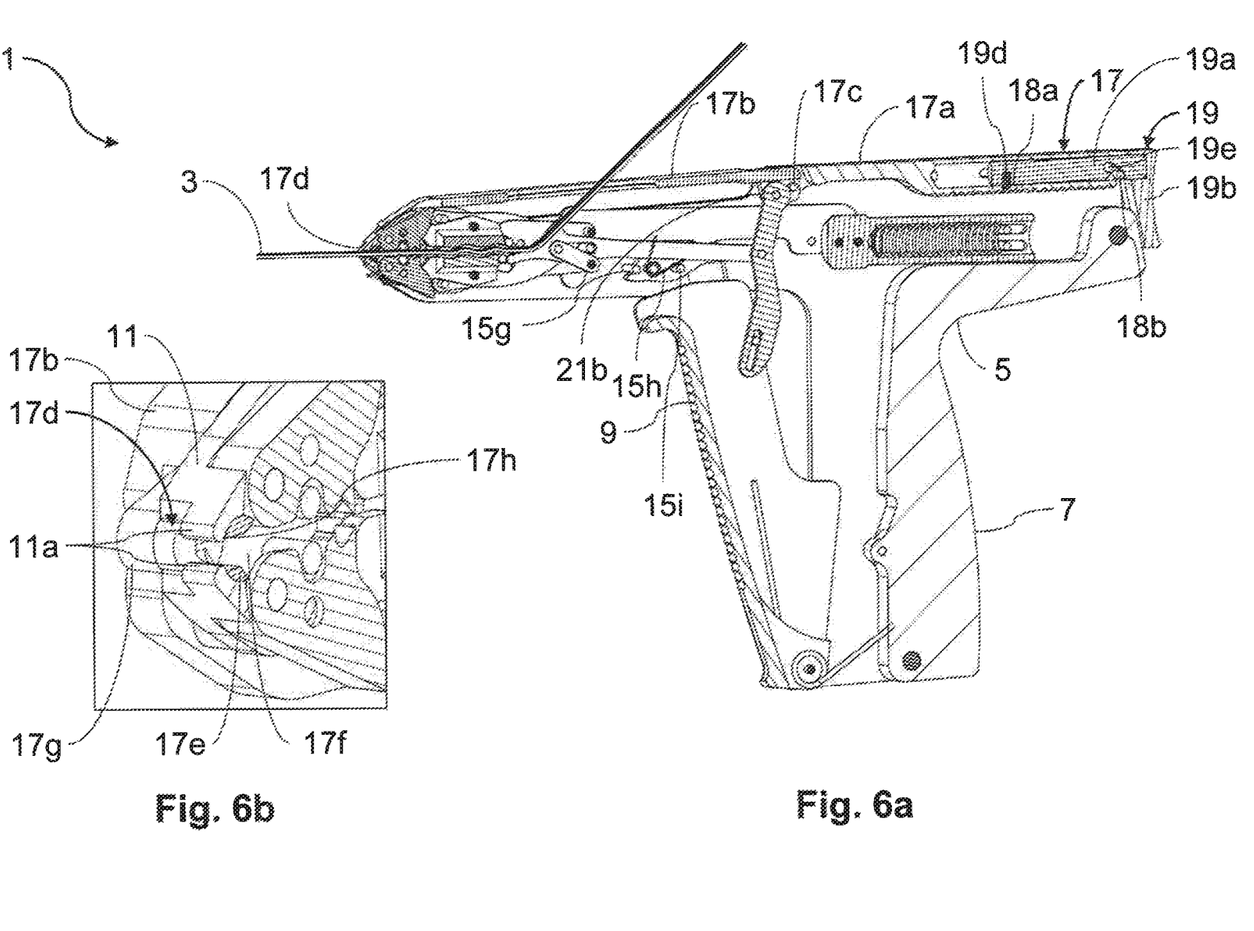
FIG. 6a is a cross-sectional view from the side of the surgical instrument in its inactive state with a cutter being released from an inoperable state by a holding member.
FIG. 6b is an enlarged perspective cross-sectional view of the front of the surgical instrument and of a cutter head in an initial state shown in FIG. 6a and any one of the preceding figures.

FIG. 6a shows the cutter 17 which comprises a longitudinal handling lever 17a hinged on one end thereof to the top axis 21b of the lever 21 to the body 5 such that it can be pivoted about the top axis 21b. In the state shown in FIG. 6a, the handling lever 17a is held fixed to the body 5 by the holding member 19.

The holding member 19 is movable relative to and guided by the handling lever 17a. In particular, the holding member 19 comprises a first portion 19a, which is at least partially guided inside the handling lever 17a, and a second portion 19b, which is exposed from the handling lever 17a at the other end of the handling lever 17a opposite to the top axis 21b. The first and second portions 19a and 19b are fixed to each other. The first portion 19a is prestressed by means of a resilient member 19c—such as the coil spring shown in FIG. 5a—inside and by the handling lever 17a in the direction of the handling lever 17a opposite the top axis 21b, while the range of motion of the first portion 19a relative to the handling lever 17a is limited by the handling lever 17a—here by means of a pin 19d extending from the first portion 19a and being enclosed in a long hole 18a of the handling lever 17a extending in the longitudinal direction of the handling lever 17a. The holding member 19 comprises an indentation 19e, which in the initial state of the handling lever 17a engages a locking pin 18b fixed to the body 5. In order to bring the handling lever 17a out of its initial state engaged to the handling lever 17a, the holding member 19 is configured to be pushed by the second portion 19b towards the handling lever 17a. Of course, a pulling or different kind of motion is also possible, as long a force against the resilient member is exerted that is capable of disengaging the holding member 19 and with it the handling lever 17a from the body 5. Only then the actual cutting operation described below can be performed.

At a portion between a center of the handling lever 17a and the end connected to the axis 21b a longitudinal transmission lever 17b is hinged to the handling lever 17a, in particular a back of the transmission lever 17b being hinged to the handling lever 17a by means of a lateral transmission axis 17c, which is closer to the axis 21b of the handling lever 17a than to the center of the handling lever 17a.

FIG. 6b shows that the front of the transmission lever 17b is hinged to a cutting head 17d held rotary in the receiving member 11. By means of the handling lever 17a, the longitudinal transmission lever 17b and the cutting head 17d, a multi-lever-assembly 17a, 17b, 17d is provided which connects the handling lever 17a and the cutting head 17d to achieve a mechanical advantage by amplifying a force exerted on the handling lever 17a to a cutting force of a cutting edge 17h of the cutting head 17d. In particular, the rotational movement of the handling lever 17a is transformed into a translational movement of the longitudinal transmission lever 17b as part of a first lever stage, and the translational movement of the longitudinal transmission lever 17b is transformed into a rotational movement of the cutting head 17d as part of a second lever stage. The longitudinal transmission lever 17b comprises the second opening B, see FIG. 2a.

The cutting head 17d has a cylinder portion 17e with a Y-shaped cut-through opening 17f. In the state shown in FIGS. 6a and 6b, this Y-shaped cut-through opening 17f has an orientation in which the leg of the Y-shaped cut-through opening 17f points to the front of the body 5 and the receiving member 11 in order to allow the bone fixation member 3 to be passed through from the outside of the surgical instrument 1 and to the inside of the surgical instrument 1. At both ends of the cylinder portion 17e cutting head protrusions 17g extend in parallel therefrom and hinge the transmission lever 17b on their respective ends away from the cylinder portion 17e. The opening 17f through the cylinder portion 17e creates the sharp cutting edge 17h for a bone fixation member 3 passed therethrough as is explained below. Of course, the cylinder portion 17e may have a differently shaped cut-through opening, e.g. an I-shaped, V-shaped, T-shaped etc. opening. In the shown initial state of the cutter 17, the cutting edge 17h is stepped and hidden behind the curved mouth portion with lip-shaped protrusions 11a of the receiving member 11. In other words, the opening 17f of the cutting head 17d is collinear with the opening A of the curved mouth of the receiving member 11, and at its most narrow portion wider than the opening A of the curved mouth at its most narrow portion in a direction orthogonal to the extension of the cutting edge 17h and the longitudinal extension of the body 5.

Figure 7A:
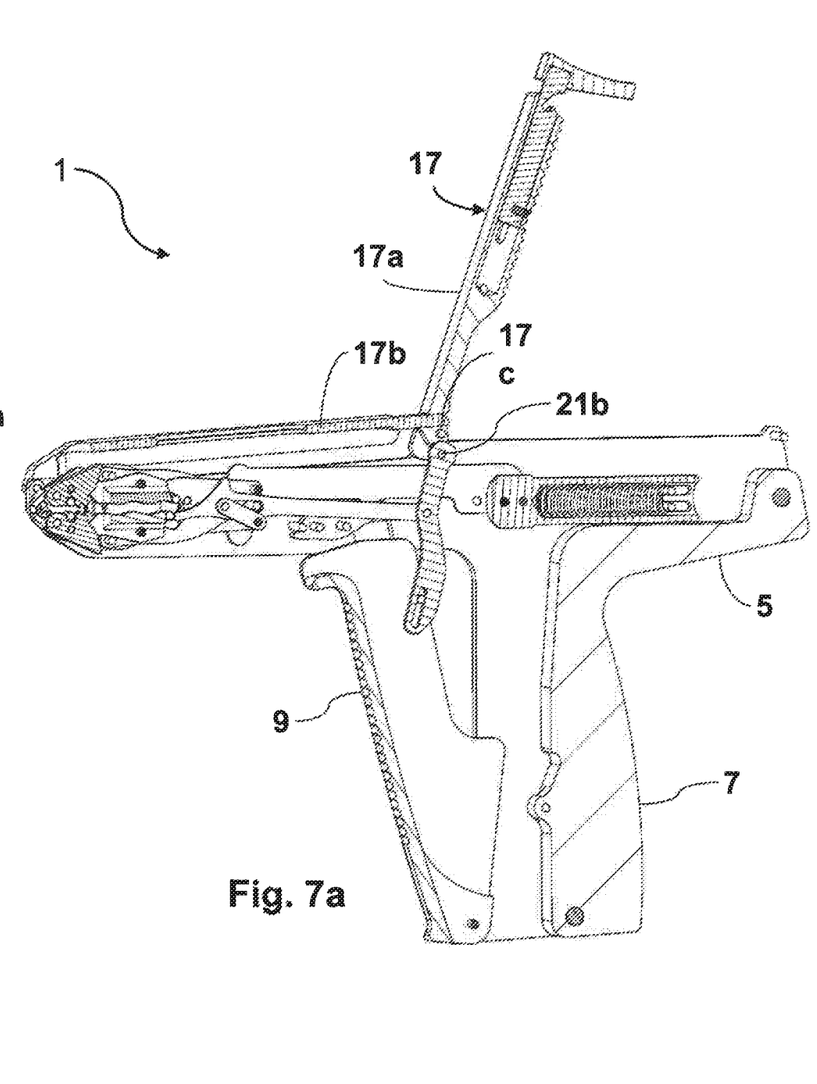
FIG. 7a is a cross-sectional view from the side of the surgical instrument in its inactive state with the cutter being operated to cut a bone fixation member (not shown)
Figure 7B:
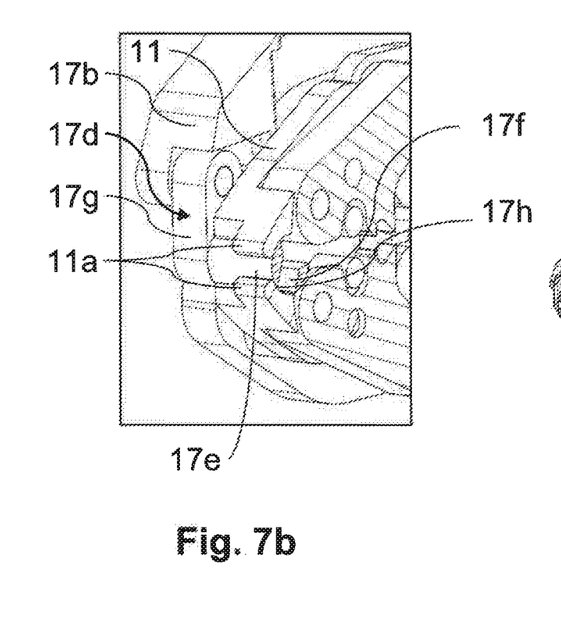

FIGS. 7a and 7b show a cutting state of the cutter 17. The handling lever 17a is pivoted counter-clockwise about the top axis 21b such that the transmission lever 17b is pushed forward in a translatory movement towards the front of the body 5.

FIG. 7b shows that the translatory displacement of the transmission lever 17b along the extension direction of the body 5 causes the cutting head 17d to rotate by pivoting its protrusions counter-clockwise about the cylinder portion 17e, wherein the cylinder portion 17e consequently is rotated within the receiving member 11. The top portion of the cylinder portion 17e with the cutting edge 17h formed by the opening 17f rotates counter-clockwise from a top to bottom direction blocking an entry opening in the receiving member 11 for a bone fixation member 3 (not shown) and cutting any bone fixation member 3 (not shown) placed therein. Of course, a rotation of the cylinder portion 17e in the opposite direction is also possible, since the bottom portion of the cylinder portion 17e may also comprise a cutting edge.

Although the present disclosure has been described in detail with reference to an exemplary surgical device 1, it should be understood that various changes, substitutions, and alterations can be made herein without departing from the invention as defined by the appended claims. The scope of the present disclosure is not intended to be limited to the particular surgical device 1 described herein.

The invention claimed is:

1. A surgical instrument for tightening a bone fixation member around bone, the surgical instrument comprising:
 a body with a gripping portion extending from the body and configured to be grasped by a hand;
 a clamp for clamping a bone fixation member, wherein the clamp comprises two opposed clamping jaws;
 a link connected to and movably guided relative to the body, wherein the clamp is connected to and movably guided relative to the link; and
 an actuator connected to and movably guided relative to the body and configured to be operated by a hand, wherein the actuator is mechanically linked to the clamp such that the actuator is configured to first move the clamp before moving the link, wherein each clamping jaw is configured to be movable by the actuator towards and/or away from the other clamping jaw.

2. The surgical instrument according to claim 1, wherein the clamp is configured to be opened and/or closed by movement of the actuator while the link remains stationary relative to the body.

3. The surgical instrument according to claim 1, wherein the clamping jaws have opposed clamping surfaces which are correspondingly shaped in a non-planar manner.

4. The surgical instrument according to claim 1, wherein the clamping jaws are configured to provide frictional engagement with a bone fixation member.

5. The surgical instrument according to claim 1, wherein the surgical instrument is configured to amplify a force transmitted from the actuator to the clamping jaws by mechanical advantage.

6. The surgical instrument according to claim 1, wherein the clamp comprises clamping arms and each of the clamping jaws is pivotably hinged on one of the clamping arms.

7. The surgical instrument according to claim 6, wherein a first end of the clamping arms, being hinged by first axes on a lever arm, is configured to be pivoted by the lever arm about a second end of the clamping arms, being hinged by second axes on the link.

8. The surgical instrument according to claim 7, wherein the clamping jaws are hinged on the clamping arms by intermediate axes which are closer to the second axes than to the first axes.

9. The surgical instrument according to claim 1, comprising a ratchet mechanism, which is connected to and movably guided relative to the body and prestressed in a direction for engaging a bone fixation member.

10. The surgical instrument according to claim 9, wherein the link is movably guided relative to the ratchet mechanism and prestressed towards the ratchet mechanism, such that in its initial non-operated state, the link is configured to be in an initial position in which it abuts the ratchet mechanism and holds it in a given position against the prestress force of the ratchet mechanism.

11. The surgical instrument according to claim 1, wherein a first end of the actuator is hinged on the gripping portion and a second end of the actuator opposite the first end is configured to be pivoted relative to the gripping portion, wherein the second end of the actuator is movably connected to a lever, which is hinged on the body by an axis and connected to the clamp.

12. The surgical instrument according to claim 1, wherein the body comprises a receiving member configured to provide an abutment surface for one portion of a bone fixation member and guide another portion of the bone fixation member towards the clamp.

13. The surgical instrument according to claim 1, further comprising:
 a limiting mechanism configured to engage the link in order to limit its range of motion relative to the body in a direction towards a bone fixation member receiving end of the body, when the link is moved a given distance relative to the body away from the bone fixation member receiving end of the body.

14. A surgical instrument for tightening a bone fixation member around bone, the surgical instrument comprising:
 a body with a gripping portion extending from the body and configured to be grasped by a hand;
 a clamp for clamping a bone fixation member;
 a link, wherein the clamp is connected to and movably guided relative to the link, wherein the link is connected to and movably guided relative to the body along the body to and away from a bone fixation member receiving end of the body;
 an actuator connected to and movably guided relative to the body and configured to be operated by a hand to move the clamp and the link relative to the body;
 a limiting mechanism configured to engage the link in order to limit a range of motion of the link relative to the body in a direction towards the bone fixation member receiving end of the body, when the link is moved a given distance relative to the body away from the bone fixation member receiving end of the body; and
 wherein the body comprises a lateral opening through which the limiting mechanism protrudes in order to be displaced from its engagement, the limiting mechanism configured to be displaced by a hand, wherein the limiting mechanism is configured to be pushed towards at least one of the gripping portion and the link for disengagement.

15. The surgical instrument according to claim 14, further comprising:
a ratchet mechanism for engaging a bone fixation member, wherein the ratchet mechanism is movable between a first bone fixation member engagement position and a second bone fixation member disengagement position, wherein the link is prestressed against the ratchet mechanism, holding the ratchet mechanism in its second position, and wherein the limiting mechanism is configured to engage the link, when the link is moved away from the ratchet mechanism by a distance, allowing the ratchet mechanism to move to its first position.

16. The surgical instrument according to claim 14, wherein the limiting mechanism is configured to be manually moved out of engagement with the link.

17. A surgical instrument for cutting a bone fixation member, the surgical instrument comprising:
- a body with a gripping portion configured to be grasped by a hand, wherein the body has a bone fixation member receiving end;
- a cutter for cutting a bone fixation member extending through the bone fixation member receiving end into the body, wherein the cutter comprises a cutting head with a cutting edge and a handling lever connected to the cutting head to actuate the cutting head, wherein one end of the handling lever is hinged on the body and the other end is free to be grasped by a hand;
- a multi-lever-assembly connecting the handling lever and the cutting head and configured to achieve mechanical advantage for an amplified cutting force of the cutting edge;
- a holding member movably attached to the handling lever and configured to hold the handling lever to the body, wherein the holding member is configured to engage the body and engage and disengage the handling lever to enable cutting; and
- an actuator connected to and movably guided relative to the body and configured to be operated by a hand to move a clamp, wherein the handling lever and the actuator are two separately moveable members to be operated by hand.

* * * * *